(12) United States Patent
Miller (10) Patent No.: US 9,815,682 B2
(45) Date of Patent: Nov. 14, 2017

(54) DISCHARGE SYSTEM AND METHODS OF DISCHARGING A CHEMICAL

(71) Applicant: Heartland Industrial Services, LLC, St. Louis, MO (US)

(72) Inventor: Harry James Miller, Belton, MO (US)

(73) Assignee: Heartland Industrial Services, LLC, St. Louis, MO (US)

( * ) Notice: Subject to any disclaimer, the term of this patent is extended or adjusted under 35 U.S.C. 154(b) by 13 days.

(21) Appl. No.: 14/939,330

(22) Filed: Nov. 12, 2015

(65) Prior Publication Data
US 2016/0137484 A1    May 19, 2016

Related U.S. Application Data

(60) Provisional application No. 62/079,089, filed on Nov. 13, 2014.

(51) Int. Cl.
| | |
|---|---|
| *B67D 7/02* | (2010.01) |
| *B67D 7/58* | (2010.01) |
| *B67D 7/78* | (2010.01) |
| *C12P 19/14* | (2006.01) |
| *B01J 4/00* | (2006.01) |

(52) U.S. Cl.
CPC ............ *B67D 7/0266* (2013.01); *B01J 4/008* (2013.01); *B67D 7/78* (2013.01); *C12P 19/14* (2013.01)

(58) Field of Classification Search
CPC . B67D 7/78; B67D 7/0266; B67D 7/58; B01J 4/008; C12P 19/14
See application file for complete search history.

(56) References Cited

U.S. PATENT DOCUMENTS

| | | | | |
|---|---|---|---|---|
| 3,636,831 A | * | 1/1972 | Davin | E01C 19/185 404/104 |
| 4,396,824 A | * | 8/1983 | Fiegl | B22D 41/50 137/341 |
| 4,691,842 A | * | 9/1987 | Foures | B67D 1/04 222/1 |
| 4,856,680 A | * | 8/1989 | Sitton | B67D 1/04 222/130 |
| 5,417,346 A | | 5/1995 | Ferri | |
| 5,964,378 A | | 10/1999 | Sperry | |
| 6,168,048 B1 | * | 1/2001 | Xu | B67D 1/045 222/1 |
| 7,114,517 B2 | * | 10/2006 | Sund | G01F 1/8413 137/486 |
| 8,875,950 B2 | | 11/2014 | Hayduk | |

\* cited by examiner

*Primary Examiner* — Frederick C Nicolas
(74) *Attorney, Agent, or Firm* — Stinson Leonard Street LLP (57) ABSTRACT

A system for discharging a chemical from a drum that is coupled to a drum retainer is provided. The system includes a booth having a floor, a ceiling, and walls defining an enclosure therein and configured to enclose the drum and the drum retainer. A first gas source is coupled to the booth and in flow communication to the enclosure and configured to discharge a first inert gas into the enclosure. A second gas source is coupled in flow communication to the drum and configured to discharge a second inert gas into the drum and to pressurize the chemical. The system further includes a pump coupled in flow communication to the drum and configured to discharge the chemical from the drum under at least one predetermined characteristic and out of the enclosure.

19 Claims, 6 Drawing Sheets

DISCHARGE SYSTEM AND METHODS OF DISCHARGING A CHEMICAL

CROSS-REFERENCE TO RELATED APPLICATION

This non-provisional application claims priority to U.S. Provisional Patent Application Ser. No. 62/079,089, filed on Nov. 13, 2014, which is hereby incorporated by reference in its entirety.

BACKGROUND

The embodiments described herein relate to a chemical discharge system, and more particularly, to methods and systems for discharging volatile chemicals stored in a drum connected to a drum retainer.

Plants are often used as a source for starch, which can be processed to produce ethanol and other products. Plant starches are generally in a granular form and are initially collected from plant grains using a wet milling, a dry milling, or a dry grind process. To produce ethanol, starch containing fractions derived from these processes are hydrolyzed into fermentable sugars which are then fermented to make ethanol. Several plant starch processing methods exist including a raw starch process, which involves a high temperature hydrolysis of starch frequently referred to as "liquefaction". In some starch processing facilities, a particular catalyst chemical such as, for example only, phosphorus oxychloride may be used. Typically, the volume amount needed for the catalyst chemical may not warrant an on-site storage facility to store the catalyst chemical for an extended time period. Moreover, the volatile nature of the catalyst chemical may prohibit long term, on-site storage at some processing facilities. Accordingly, in some processing facilities, the catalyst chemical may be shipped on a transport such as, for example, a cargo truck or a railcar, to the starch processing facility.

Conventionally, a drum is filled with the catalyst chemical, and the drum is connected to or fitted to a drum retainer, wherein the drum retainer is transported to the processing facility by the transport. At the processing facility, a worker wears a hazardous waste suit and unloads the drum retainer from the transport. While wearing the hazardous waste suit, the worker removes the drum from the drum retainer for subsequent connection of the drum to facility piping. Removing the drum from the drum retainer and/or moving drum may lead to safety issues such as spillage, worker hazardous exposure, and/or mishandling of the drum.

Some processing facilities place the drum at an exterior location due to the volatile nature of the catalyst chemical. Exterior storage of the drum may lead to exposure, spillage, contamination, and/or other safety issues. Moreover, the worker may deposit the drum at a location exterior to the facility which may lead to other hazardous situations such as impact by a facility forklift. Further, exterior storage of the drum may lead to increased piping, insulation, and controls to discharge the catalyst chemical into the processing facility.

DRAWINGS

These and other features, aspects, and advantages will become better understood when the following detailed description is read with reference to the accompanying drawings in which like characters represent like parts throughout the drawings, wherein.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

The embodiments described herein relate to systems and methods of discharging a chemical. More particularly, the embodiments relate to system and/or apparatus and/or method to safely, efficiently, and economically discharge a volatile chemical into a processing facility. Moreover, the embodiments relate to containing the chemical drum in an enclosure while remaining connected to a drum retainer and minimizing hazardous conditions for the worker. The embodiments described herein include a variety of types of chemicals and processing facilities, and the description and figures that utilize phosphorus oxychloride and ethanol facilities are exemplary only.

Figure 1:
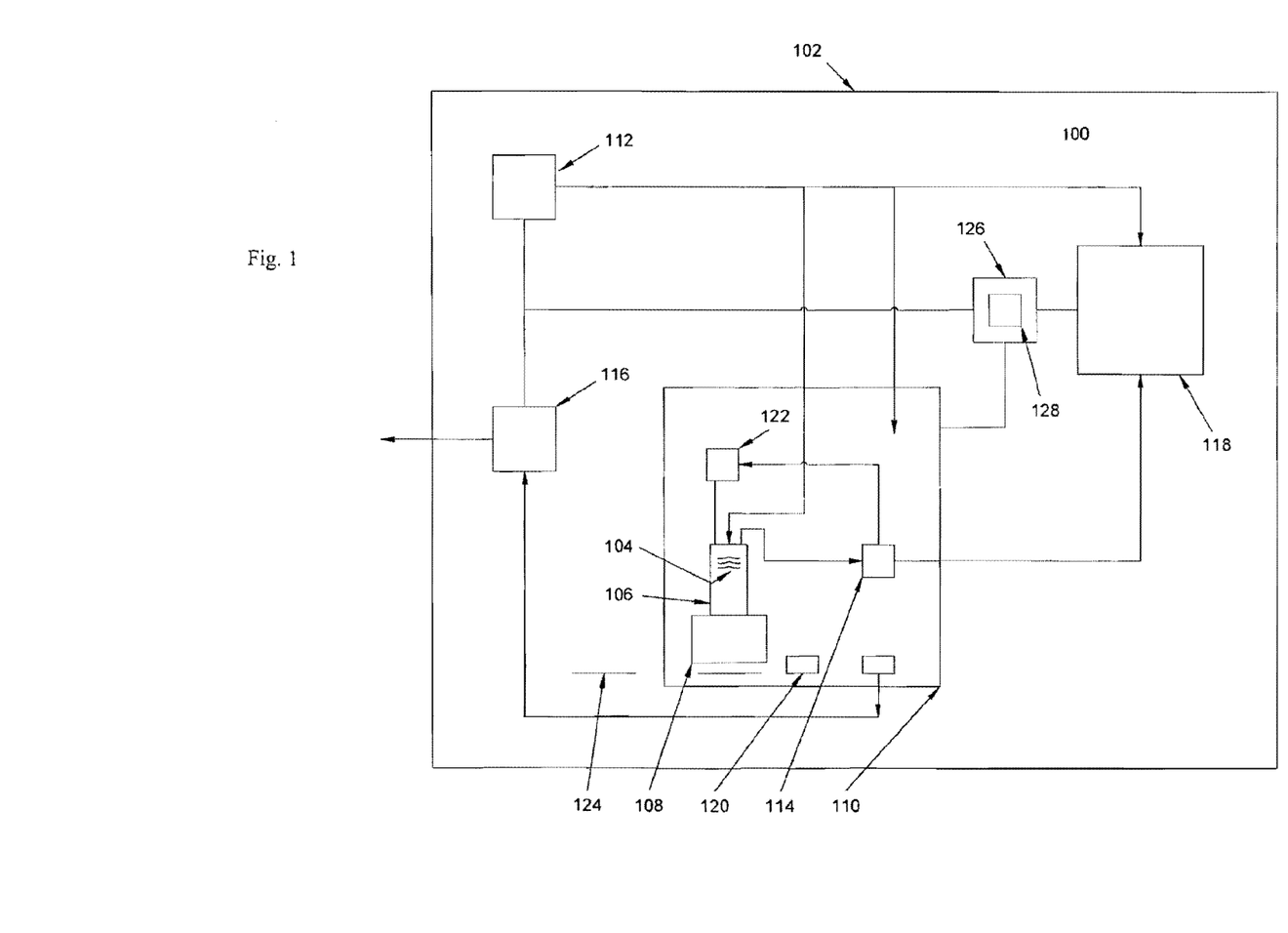
FIG. 1 is a schematic view of an exemplary chemical discharge system coupled to an associated processing facility.

FIG. 1 is schematic view of a discharge system 100 that is coupled to a chemical processing facility 102, which is configured to process a chemical 104. In the exemplary embodiment, the chemical 104 includes a hazardous and volatile chemical such as, but not limited to, phosphorus oxychloride, while the processing facility 102 includes an ethanol processing facility. Alternatively, the chemical 104 may include any composition and the processing facility may include any facility for processing any chemical. The chemical 104 is stored within a drum 106, wherein the drum 106 is coupled to a drum retainer 108. The drum 106 is fixedly coupled to the drum retainer 108 such that the drum 106 remains connected to the drum retainer 108 during chemical discharge operations. More particularly, the drum 106 remains coupled to the drum retainer 108 to facilitate safe, convenient, and economical processes such as unloading, transporting, and loading the drum 106 and discharging the chemical 104 relative to the processing facility 102.

In the exemplary embodiment, the discharge system 100 includes a booth 110, a gas system 112, a pump system 114, and an exhaust system 116. Moreover, the discharge system 100 includes a storage facility 118, a heat transfer system 120, a calibration system 122, and a conveyor system 124 coupled to the booth 110. A control system 126 that is coupled to the systems and includes a controller 128 that is configured to operatively control handling of the drum 106 and discharge of the chemical 104 from the drum 106 and into the processing facility 102. The discharge system 100 may include a variety of piping such as schedule 40 carbon steel and 316 stainless steel with associated welded and/or threaded piping connections. The discharge system 100 may include a plurality of components such as, but not limited to, regulators, valves, solenoids, actuators, and flow sensors.

Figure 2:
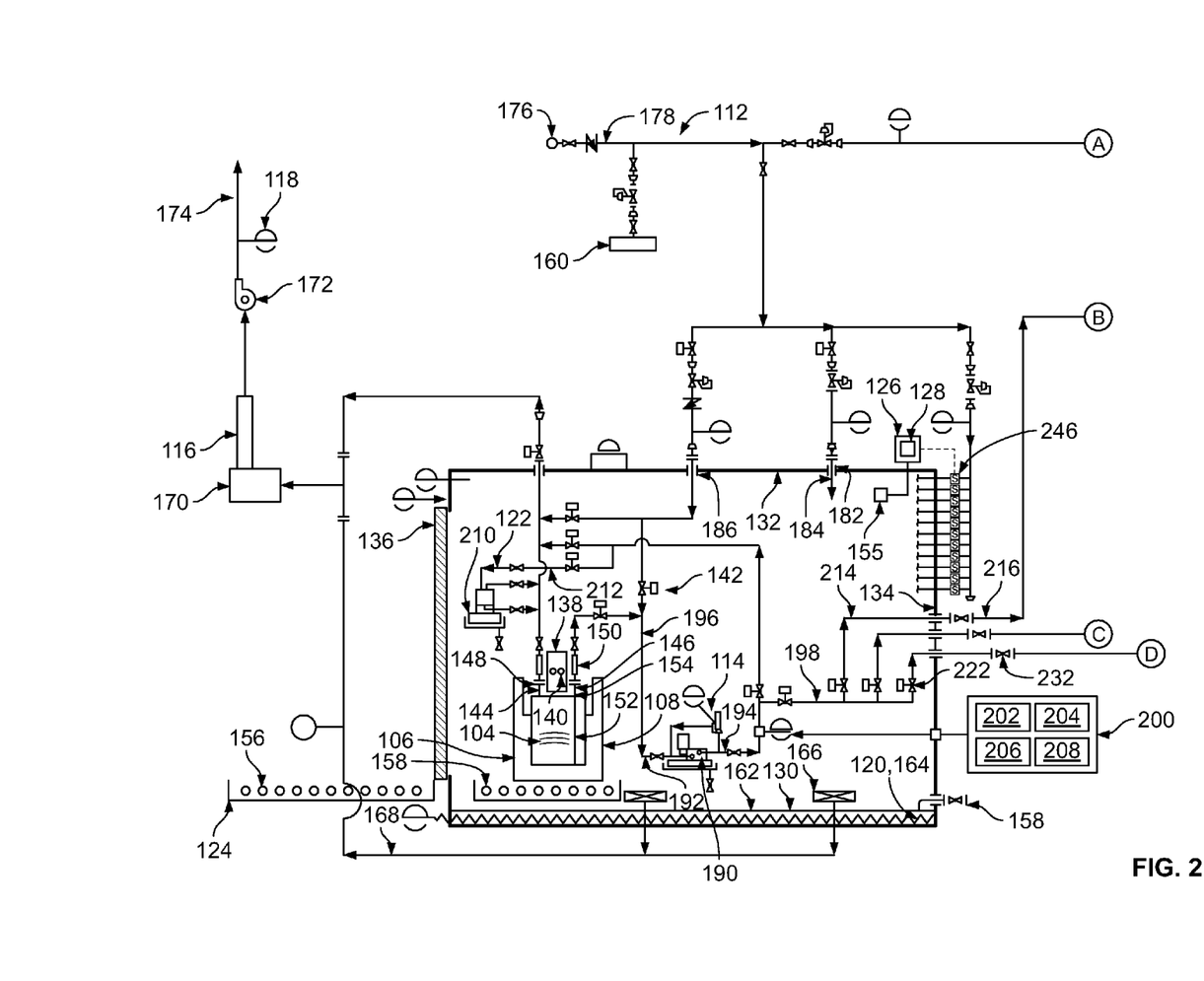
FIG. 2 is a schematic view of an exemplary booth, a gas system, a pump system, an exhaust system, a conveyor system, and a storage facility of the chemical discharge system shown in FIG. 1.

FIG. 2 is a schematic view of the booth 110, the gas system 112, the pump system 114, the exhaust system 116, and the conveyor system 124. In the exemplary embodiment, the booth 110 includes a floor 130, a ceiling 132, and sidewalls 134, wherein a sealable door 136 is coupled to one of the sidewalls 134. Moreover, at least one sidewall includes a window 138 and a pair of glove access ports 140 defined through the window 138 and/or sidewall 134. In the exemplary embodiment, the window 138 includes a grade of material such as explosion proof and/or bullet proof glass. Alternatively, the window 138 may include other materials such as, for example, plastic.

The floor 130, ceiling 132, and sidewalls 134 are coupled together to define an enclosure 142 for housing the drum 106 and the drum retainer 108. In the exemplary embodiment, the floor 130, ceiling 132, sidewalls 134, and the door 136 include chemically resistant materials such as stainless steel and nickel. Moreover, the door 136 includes a chemically resistant material such as ethylene propylene diene monomer or Viton®. Alternatively, the floor 130, ceiling 132, sidewalls 134, and the door 136 may include any material composition to withstand effects of the chemical 104 stored in the drum 106. The drum 106 includes a 55 gallon drum with an over pack and is configured to contain and store the chemical 104. The drum 106 further includes an inlet port 144 and an outlet port 146. Ports 144 and 146 may include flange connectors 148 and flex hoses 150 to facilitate coupling in flow communication to components of the discharge system 100. The outlet port 146 further includes a dip tube 152 which may have a bung mount 154.

The booth 110 includes a length of having a range of about 5 feet to about 30 feet; a width having a range from about 5 feet to about 30 feet; and, a height having a range from about 5 feet to about 30 feet. More particularly, the booth 110 has a length of about 8 feet, a width of about 8 feet, and a height of about 8 feet. The booth 110 is sized and shaped to safely, efficiently, and economically couple to the processing facility 102 while housing the drum 106 and the drum retainer 108. Further, the booth 110 is sized and shaped to meet and/or maintain and/or exceed safety and environmental standards. Moreover, the booth 110 is configured to maintain a controllable environment for the enclosure 142 to facilitate handling and discharging of the chemical 104 from the drum 106 and into the chemical processing facility 102. In the exemplary embodiment, the booth 110 can be built and/or installed within the existing processing facility 102. Alternatively, the booth 110 can be used as a mobile and/or portable unit that can be removably coupled to the existing processing facility 102. The booth 110 includes a pressure interlock system 155 with gas sensors or pressure sensors (not shown) that are operatively coupled to the controller 128. The gas sensors/pressure sensors are configured to sense, or measure any gas, such as nitrogen, present within the enclosure 142. When a particular gas is sensed within the enclosure 142, the pressure interlock system 155 is configured to lock the door 136 to prevent access within the booth 110 for safety and emissions considerations. Moreover, the sensors can sense any leakage of the gas from the booth 110 and produce an alarm to notify of gas leakage from the booth 110.

The conveyor system 24 is coupled to the booth 110 and to the control system 126. The conveyor system 124 includes a first conveyor 156 that is positioned exterior of the booth 110 and a second conveyor 158 that is positioned within the enclosure 142. In the exemplary embodiment, the first conveyor 156 and the second conveyor 158 include roller conveyors rated for about 1000 pounds and made from chemically resistant materials such as 316 stainless steel. Alternatively, the first conveyor 156 and the second conveyor 158 can include any configuration, size, rating, and material composition to facilitate moving the drum retainer 108 safely and efficiently into and out of the enclosure 142. Moreover, the first conveyor 156 and the second conveyor 158 can be manually operated or automatically operated.

The first conveyor 156 is configured to receive the drum retainer 108 with the attached drum 106 from a transport (not shown), for example, a cargo truck or a railcar. Moreover, the first conveyor 156 is configured to facilitate moving the drum retainer 108 from the transport and through the open door 136. The second conveyor 158 is configured to receive the drum retainer 108 from the first conveyor 156 and to facilitate moving the drum retainer 108 through the door 136 and into the enclosure 142. Subsequent chemical discharge, the second conveyor 158 is configured to transport the drum retainer 108 out of the booth 110 and onto the first conveyor 156. The first conveyor 156 and the second conveyor 158 are configured to safely, efficiently, and economically transport the drum retainer 108 with the attached drum 106 during chemical discharge operations. For an automatic operation, the controller 128 is operatively copied to at least one of the first conveyor 156 and the second conveyor 158 to selectively operate the first conveyor 156 and/or the second conveyor 158 for safely, efficiently, and economically moving the drum 106 and the drum retainer 108.

The heat transfer system 120 is coupled to the booth 110 and to the control system 126. More particularly, the heat transfer system 120 is coupled to booth 110 and in between the floor 130 and a base 162. The heat transfer system 120 includes a resistive heat element 164 that is configured to heat the enclosure 142. Alternatively, the heat transfer system 120 may include other configurations such as forced air systems and fluid systems (for example heat pipes). The heat transfer system 120 is configured to maintain the temperature of the enclosure 142 between about 55 degrees Fahrenheit (0 F) to about 750 F. More particularly, the heat transfer system 120 is configured to maintain the temperature within the enclosure 142 at about 680 F. Alternatively, the heat transfer system 120 can be configured to maintain any temperature within the enclosure 142. The heat transfer system 120 may include any configuration to transfer heat into and/or out of enclosure 142 to facilitate maintaining a controlled temperature environment within the enclosure 142. The controller 128 is operatively coupled to the heat transfer system 120 and is configured to provide a controlled temperature environment for the enclosure 142. The controlled temperature environment facilitates maintaining the chemical 104 stored in the drum 106 at a predetermined temperature to facilitate safe, efficient, and economical discharge of the chemical 104 from the drum 106 and into the processing facility 102.

The exhaust system 116 is coupled to the booth 110 and the controller 128, and in flow communication to the enclosure 142. The exhaust system 116 includes vents 166 coupled to at least one of the floor 130, the ceiling 132, and the sidewalls 134. Moreover, the exhaust system 116 includes a duct 168 coupled to the vents 166 and coupled to a scrubber 170 and blower/fan assembly 172. The scrubber 170 is configured to clean, filter, and/or purge the contents of the enclosure 142 prior to release to the atmosphere 174. The blower 172 is configured to force the contents such as, but not limited to, air, inert gas, contaminants, out of the enclosure 142 for discharge to the atmosphere 174. In the exemplary embodiment, the blower 172 includes, for example only, a 150 cubic feet per minute fan blower. The exhaust system 116 includes at least one sensor that is configured to sense and measure gases flowing through vents 166 and/or duct 168. When gas measurements are high, such as elevated oxygen levels, the exhaust sensor is configured to indicate a leak in the booth 100, wherein the leak is pulling additional air into the booth 110. The exhaust system 116 is configured to alert the controller 128 regarding the sensed leak. The controller 128 is configured to shut down a component such as, but not limited to, the pump system 114 in response to leak notification.

The gas system 112 is coupled in flow communication to the processing facility 102 such at, for example, an existing gas header 176. In the exemplary embodiment, the gas system 112 includes a primary gas source 178 coupled in flow communication to the gas header 176 by a valve assembly such as a ball valve and check valve combination. The primary gas source 178 is configured to discharge inert gas 184 through the discharge system 100. The gas system 112 further includes a secondary gas source 180 such as, but not limited to, a removable gas bottle. The removable secondary gas source 180 is coupled in flow communication to the processing facility 102 to facilitate providing additional supply of inert gas 184 and/or a backup supply of inert gas 184 to the gas system 112. Alternatively, for processing facilities that do not have an existing gas header 176, the secondary gas source 180 provides the required inert gas 184 needed to discharge the chemical 104 from the drum 106 as described herein.

The primary gas source 178 further includes a first inlet 182 coupled to the booth 110 and in flow communication to the enclosure 142. The primary gas source 178 is configured to discharge the inert gas 184 such as, for example only, nitrogen from the gas header 176 and/or from the removable gas source 180 and toward the first inlet 182. The first inlet 182 is configured to discharge the inert gas 184 into the enclosure 142 to displace air through the vents 166 and out of the enclosure 142. Moreover, the first inlet 182 is configured to discharge the inert gas 184 into the enclosure 142 to purify the enclosure 142 and maintain a predetermined internal pressure within the enclosure 142. In the exemplary embodiment, the first inlet 182 is configured to discharge inert gas 184 into the enclosure 142 and to maintain the enclosure 142 at a pressure range from about 1 pound per square inch (psi) to about 5 (psi). Alternatively, the first inlet 182 is configured to discharge the inert gas 184 at any pressure range within enclosure 142 to enable the discharge system 100 to function as described herein. Moreover, pumping air out of the enclosure 142 facilitates providing an inert environment within the enclosure 142. The inert environment within the enclosure 142 reduces and/or eliminates react ability of the chemical 104 if the chemical 104 is exposed within the enclosure 142 such as by, for example, leakage from the drum 106.

The primary gas source 178 further includes a second inlet 186 coupled in flow communication to the inlet port 144 of the drum 106. The primary gas source 178 is configured to discharge the inert gas 184 from the gas header 176 and/or from the removable gas source 180 and towards the second inlet 186. The second inlet 186 is configured to discharge the inert gas 184 through the inlet port 144 and into the drum 106. Discharging the inert gas 184 from the second inlet 186 and into the drum 106 pressurizes the chemical 104 within the drum 106 to facilitate discharge of the chemical 104 from the drum 106. In the exemplary embodiment, the second inlet 186 is configured to discharge the inert gas 184 into the drum 106 at a pressure range from about 1 psi to about 100 psi. More particularly, the second inlet 186 is configured to discharge the inert gas 184 into the drum 106 and maintain the chemical 104 within the drum 106 at a pressure of about 50 psi. Alternatively, the second inlet 186 is configured to discharge the inert gas 184 into the drum 106 at any pressure range to enable discharge of the chemical 104 from the drum 106 as described herein. Further, the second inlet 186 is coupled in flow communication to the exhaust system 116. The second inlet 186 is configured to discharge the inert gas 184 through the exhaust system 116 to facilitate purging the exhaust system 116 and/or the pump system 114. The controller 128 is operatively connected to the gas system 112 and is configured to selectively operate the gas system 112 for safe, efficient, and economical discharging of the inert gas 184 throughout the discharge system 100.

In the exemplary embodiment, the pump system 114 is coupled to the booth 110 and in flow communication to the drum 106. More particularly, the pump system 114 is coupled to the booth 110, for example at the side wall, and suspended from the floor 130. Suspending the pump system 114 from the floor 130 facilitates preventing or eliminating any contact with the chemical 104 should the chemical 104 leak from the drum 106 and onto the floor 130. The booth 110 floor 130 and/or sidewall includes an emergency clean out opening 188 and associated valve to facilitate draining any leaked or spilled chemical 104 out of the booth 110. In an embodiment, the pump system 114 includes, for example only, a metering pump 190 having a pump inlet 192 and a pump outlet 194. The metering pump 190 includes operating parameters such as a three phase, 0.5 horsepower, 230 volt while operating at 40 gallons per hour at 50 psi using a variable frequency drive. Alternatively, the metering pump 190 can include any configuration, size, rating, and operating parameter to enable the pump system 114 to operate as described herein.

The pump system 114 includes inlet piping 196 coupled with in flow communication to the outlet port 146 and the pump inlet 192. The inlet piping 196 may also be coupled in flow communication to the second inlet 186 for inert gas purging of the pump system 114. Moreover, the pump system 114 includes outlet piping 198 coupled in flow communication to the pump outlet 194 and the storage facility 118. To control flow of inert gas 184, valves may be used to isolate the inlet piping 196 coupled to the second inlet 186 and to isolate the outlet piping 198 coupled to the storage facility 118. The pump 190 is configured to pump pressurized chemical 104 from the drum 106, through the outlet port 146, and into the pump inlet 192. The pump 190 is further configured to pump the chemical 104 from the pump inlet 192, through the pump outlet 194, and into the outlet piping 198 under at least one of a controlled and predetermined characteristic 200 such as, but no limited to, a temperature 202, a specific gravity 204, a flow rate 206, and a pressure 208 of the discharged chemical 104. The discharge system 100 is configured to form the predetermined characteristic 200 to provide a safe, efficient, and economical delivery of the chemical 104 out of the drum 106 and into the storage facility 118.

In the exemplary embodiment, the discharged chemical 104 includes the predetermined characteristic 200 of the temperature 202 having a range from about 40° F. to about 100° F. More particularly, the temperature 202 of the discharged chemical 104 is about 70° F. Moreover, the discharged chemical 104 has the predetermined characteristic 200 of the specific gravity 204 having a range from about 1.6 to about 1.7. More particularly, the specific gravity 204 of the discharged chemical 104 is about 1.675. Still further, the discharged chemical 104 has the predetermined characteristic 200 of the flow rate 206 from the drum 106 having a range from about 0.5 pounds per hour (lb./hr.) to about 2000 lb./hr. More particularly, the flow rate 206 has a range from about 0.5 lb./hr. to about 10 lb./hr. Moreover, in an embodiment, the flow rate 206 has a range from about 0.5 ft./sec. to about 10 ft./sec. In an embodiment, the discharged chemical 104 includes the predetermined characteristic 200 of pressure 208 having a range from about 5 psi to about 80 psi. More particularly, the pressure 208 is about 60 psi. The predetermined characteristic 200 includes the temperature 202, the specific gravity 204, the flow rate 206 and the pressure 208 to enable safe, efficient, and economical discharge of the chemical 104 from the drum 106 and into the processing facility 102 while the drum 106 remains attached to the drum retainer 108. Alternatively, the predetermined characteristic 200 may include any temperature 202, specific gravity 204, flow rate 206 and pressure 208 to enable safe, efficient, and economical discharge of the chemical 104 from the drum 106 and into the processing facility 102 while the drum 106 remains attached to the drum retainer 108. The controller 128 is operatively coupled to the pump system 114 and is configured to selectively operate the pump 190 for safely, efficiently, and economically pumping the discharged chemical 104 at the predetermined characteristics 200.

The calibration system 122 is coupled in flow communication to and located between the outlet piping 198 and the inlet port 144. The calibration system 122 is coupled to the booth 110, for example at the side wall, and suspended from the floor 130. Suspending the calibration system 122 from the floor 130 facilitates preventing or eliminating any contact with the chemical 104 should the chemical 104 leak from the drum 106 and onto the floor 130. In the exemplary embodiment, the calibration system 122 includes a measurement device 210 such as, but not limited to, a scale, a spectrometer, a thermometer, and a flow meter. The calibration system 122 is configured to selectively receive a portion 212 of the discharged chemical 104 that is pumped through outlet piping 198. Moreover, the calibration system 122 is configured to calibrate and/or measure at least one of the predetermined characteristics 200 of the portion 212 of the discharged chemical 104 for reporting, notifying, and/or recording purposes. After receiving and/or calibrating the discharged chemical 104, the calibration system 122 is configured to discharge the portion 212 of the chemical 104 into the inlet port 144 for recirculation of the chemical 104 disposed within the drum 106. The controller 128 is operatively coupled to the calibration system 122 and is configured to selectively operate the calibration system 122 for monitoring, measuring, and/or reporting the predetermined characteristics 200 of the discharged chemical 104.

The pump outlet 194 piping includes a plurality of branches 214 such as, for example, a first branch 216, a second branch 218, and a third branch 220. Alternatively, the plurality of branches 214 can include less than or more than three branches. The plurality of branches 214 can include any number of branches to enable the discharge system 100 to function as described herein. Control valves 222 are coupled in flow communication to the plurality of branches 214 and coupled to the controller 128. The control valves 222 are selectively operable by the controller 128 to discharge the chemical 104, at the predetermined characteristics 200, selectively through at least one of the first branch 216, the second branch 218, and/or the third branch 220. The plurality of branches 214 can also be coupled in flow communication to the gas system 112 for inert gas purging of the plurality of branches 214. In the exemplary embodiment, the discharged chemical 104 has a flow rate through the plurality of branches 214 having a range from about 0.5 ft./sec. to about 10 ft./sec.

The storage facility 118 includes a plurality of storage tanks 224 such as, for example, a first storage tank 226, a second storage tank 228, and a third storage tank 230. Alternatively, the plurality of storage tanks 224 can include less than or more than three tanks. The plurality of storage tanks 224 can include any number of storage tanks to enable discharge system 100 to function as described herein. The plurality of storage tanks 224 can be permanently installed at the processing facility 102 or can be removably connected to the chemical processing facility 102 based on required processing and/or storage needs of the chemical processing facility 102. In the exemplary embodiment, the plurality of storage tanks 224 is coupled in flow communication to the plurality of branches 214. More particularly, the first storage tank 226 is coupled in flow communication to the first branch 216; the second storage tank 228 is coupled in flow communication to the second branch 218; and, the third storage tank 230 is coupled in flow communication to the third branch 220. Valves 232 such as double block valves may be coupled in flow communication to the first branch 216, the second branch 218, and the third branch 220 to facilitate shut-off or isolation capability of the first storage tank 226, the second storage tank 228, and/or the third storage tank 230, from the outlet piping 198.

The controller 128 is operatively coupled to the valves 232 and configured to operate the valves 232 for selective distribution of the chemical 104 from the plurality of branches 214 and into the plurality of storage tanks 224. In the exemplary embodiment, the valves 232 are coupled in flow communication to each storage tank 226, 228, and 230. The valves 232 are configured to discharge the chemical 104 from a selected branch and into an associated storage tank at flow rate 206 having a range from about 0.5 ft./sec. to about 10 ft./sec. The controller 128 is configured to safely, efficiently, and economically control the flow rate 206 of the discharged chemical 104 selectively into the plurality of storage tanks 224.

Figure 3:
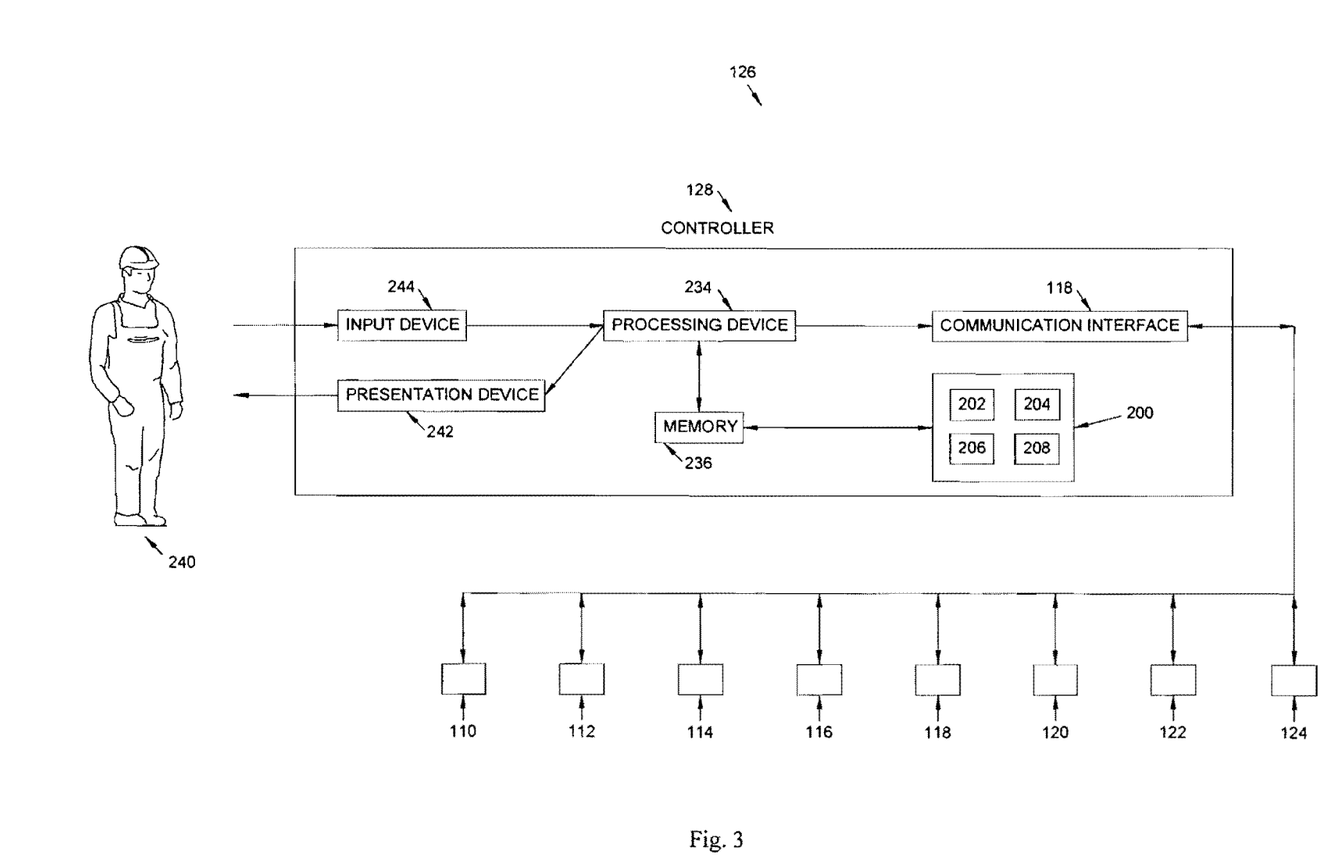
FIG. 3 is a block diagram illustrating an exemplary control system having a controller for use in controlling operation of the chemical discharge system shown in FIG. 1.

FIG. 4 is a block diagram illustrating the control system 126 having the controller 128 for use in controlling operation of the discharge system 100. The controller 128 includes a processor 234 and a memory 236. The processor 234 includes a processing unit, such as, without limitation, an integrated circuit (IC), an application specific integrated circuit (ASIC), a microcomputer, a programmable logic controller (PLC), and/or any other programmable circuit. The processor 234 may include multiple processing units (e.g., in a multi-core configuration). The controller 128 is configurable to perform the operations described herein by programming the processor 234. For example, the processor 234 may be programmed by encoding an operation as one or more executable instructions and providing the executable instructions to the processor 234 in the memory 236 coupled to the processor 234.

The memory 236 includes, without limitation, one or more random access memory (RAM) devices, one or more storage devices, and/or one or more computer readable media. The memory 236 is configured to store data, such as computer-executable instructions and pre-determined characteristics 200, such as, for example only, temperature 202, specific gravity 204, flow rate 206, and pressure 208 of the discharged chemical 104. The memory 236 includes any device allowing information, such as executable instructions and/or other data, to be stored and retrieved. Moreover, the control system 126 may include a plurality of sensors (not shown) coupled to the discharge system 100 for monitoring, measuring, and/or reporting operating conditions of the components of the discharge system 100. Stored in the memory 236 are, for example, readable instructions for controlling operations of the discharge system 100. The controller 128 includes a device interface which may include, among other structures, a web browser and/or a client application. The web browsers and the client applications enable users 240 to display and interact with media and other information. Exemplary client applications include, without limitations, a software application for managing one or more controllers.

The controller 128 includes at least one presentation device 242 for presenting information to the user 240. The presentation device 242 includes any component capable of conveying information to the user 240. The presentation device 242 includes, without limitation, a display device (not shown) (e.g., a liquid crystal display (LCD), organic light emitting diode (OLED) display, or "electronic ink" display) and/or an audio output device (e.g., a speaker or headphones). The presentation device 242 includes an output adapter (not shown), such as a video adapter and/or an audio adapter which is operatively coupled to the processor 234 and configured to be operatively coupled to an output device (not shown), such as a display device or an audio output device.

Moreover, the controller 128 includes an input device 244 for receiving input from the user 240. The input device 244 includes, for example, a keyboard, a pointing device, a mouse, a stylus, a touch sensitive panel (e.g., a touch pad or a touch screen), a gyroscope, an accelerometer, a position detector, and/or an audio input device. A single component, such as a touch screen, may function as both an output device of the presentation device 242 and the input device 244. The controller 128 can be communicatively coupled to a network (not shown).

In the exemplary embodiment, the computer-readable storage media is used for discharging the chemical 104 stored in the drum 106 that is coupled to the drum retainer 108. The computer-readable storage media includes computer-executable instructions embodied thereon. When executed by at least one processor 234, the computer-readable instructions cause the processor 234 to: discharge the inert gas 184 into the enclosure 142; discharge the inert gas 184 into the drum 106 to pressurize the chemical 104; and pump the pressurized chemical 104 under at least one predetermined characteristic 200 and out of the enclosure 142.

More particularly, the control system 126 includes a plurality of solenoid valves 246 coupled to the booth 110 and in flow communication to components of the discharge system 100. The controller 128 is configured to selectively operate the solenoid valves 246 for controlling flow of inert gas 184 to and/or from at least one of the gas system 112, the exhaust system 116, and the booth 110. Additionally, the controller 128 is configured to selectively operate the conveyor system 124, the heat transfer system 120, the pump system 114, the storage facility 118, and [the calibration system 122]. More particularly, the controller 128 is coupled to and configured to selectively operate valves of the discharge system 100 for selective discharge of the chemical 104 from the drum 106 and at the predetermined characteristics 200 while the drum 106 remains coupled to the drum retainer 108.

During an exemplary operation, the controller 128 selectively operates the booth 110, the gas system 112, pump system 114, and the exhaust system 116. Moreover, the controller 128 selectively operates the storage facility 118, the heat transfer system 120, the calibration system 122, and the conveyor system 124. The controller 128 is configured to selectively open and close the plurality of valves of discharge system 100. During operation, the door 136 is automatically or manually opened to expose the second conveyor 158 to the first conveyor 156. The drum retainer 108 with the associated drum 106 is unloaded from the cargo carrier (not shown) and onto the first conveyor 156. The first conveyor 156 moves the drum retainer 108/drum 106 through the door 136 and onto the second conveyor 158. The second conveyor 158 moves the drum retainer 108/drum 106 within the enclosure 142 and near the window 138. The door 136 is closed to safely and conveniently isolate the drum retainer 108 and the drum 106 within the booth 110. During the exemplary operation, the worker can handle the drum 106 without a hazardous material suit to increase worker maneuverability and decrease costs.

The controller 128 selectively operates the gas system 112 to direct the inert gas 184 from at least one of the primary gas source 178 and the secondary gas source 180 and through the first inlet 182. The first inlet 182 discharges the inert gas 184 into the enclosure 142 to purge the air and/or any contaminants out of the enclosure 142 and through the vents 166. The blower 172 draws the discharged air and/or contaminates through the scrubber 170 for cleaning prior to the release to the atmosphere 174. Moreover, the first inlet 182 discharges the inert gas 184 into the enclosure 142 for safely pressurizing the enclosure 142.

With the enclosure 142 purged, a worker (not shown) slips arms through the glove access ports 140 to couple the inlet port 144 in flow communication to the second inlet 186 and to couple the outlet port 146 to the inlet piping 196. Since the drum 106 remains coupled to the drum retainer 108, the worker can safely, efficiently, and economically couple the drum 106 to the gas system 112 and the pump system 114. Thus, due to at least the contained environment of the enclosure 142, a single worker without a need for a hazardous suit can move the drum 106 in to the booth 110 and connect the drum 106 to the gas system 112 and the pump system 114. Moreover, since the drum 106 remains connected to the drum retainer 108, the drum retainer 108 minimizes and/or eliminates spillage and/or damage of the drum 106 to increase safety and productivity.

The controller 128 selectively operates the second inlet 186 to direct inert gas 184 from at least one of the primary gas source 178 and the secondary gas source 180 and through second inlet 186. Since the second inlet 186 is coupled in flow communication to the drum 106 at the inlet port 144, the second inlet 186 discharges the inert gas 184 into the drum 106 to facilitate pressurizing the inert gas 184 within the drum 106. The controller 128 selectively operates the metering pump 190 to pump the chemical 104 from the drum 106, through the outlet port 146, and into the outlet piping 198. The metering pump 190 is sized and shaped to pump the chemical 104 at the predetermined characteristic 200 such as the controlled temperature 202, the controlled specific gravity 204, the controlled flow rate 206, and/or the controlled pressure 208 from the drum 106 and to the outlet piping 198. Moreover, the heat transfer system 120 regulates the temperature 202 within the enclosure 142 to facilitate regulating the controlled temperature 202 of the chemical 104.

In the exemplary embodiment, the controller 128 selectively operates the control valves 222 to direct the chemical 104 through the plurality of branches 214. The chemical 104 flows through the selected branch of the plurality of branches 214 to controllably discharge the chemical 104 to the storage facility 118. More particularly, the controller 128 selectively operates the control valves 222 to direct the chemical 104 to a selected storage tank of the plurality of storage tanks 224. While flowing through the plurality of branches 214, sensors such as flow meters and thermometers measure parameters such as temperature 202 and flow rate 204. The sensors can report the measured parameters to the controller 128 for subsequent reporting, analysis and/or adjustment. For example only, the controller 128 may open control valve and close control valves 222 to direct the chemical 104 through the first branch 216 and meter the chemical 104, at the pre-determined flow rate 206, into the first storage tank 226 for subsequent storage.

As the metering pump 190 discharges the chemical 104 from the drum 106 and into the plurality of branches 214, the controller 128 selectively opens and closes valves coupled to the outlet piping 198 to direct a portion 212 of the chemical flow to the calibration system 122. The calibration system 122 receives the portion 212 of the chemical 104 and conducts an analysis on the chemical 104. For example, the calibration scale measures the specific gravity 204, the flow rate 204, the flow volume, the chemical composition, and the temperature 202 of the chemical 104 flowing through the calibration system 122. The calibration system 122 reports the measured parameters to the controller 128 for subsequent record keeping, analysis, and/or adjustment.

After the metering pump 190 has discharged the pre-determined amount of chemical 104 into the plurality of storage tanks 224, the controller 128 may close the valves to isolate the plurality of storage tanks 224 from the gas system 112 and the pump system 114. The controller 128 may maintain valves in the plurality of branches 214 in open positions so the pump system 114 and drum 106 remain in flow communication with the gas system 112. In this position, the controller 128 instructs the gas system 112 to discharge inert gas 184 from the primary gas source 178 and/or the secondary gas source 180, through the plurality of branches 214 and through the metering pump 190 to backflow any chemical 104 present in the branches 214 back through the metering pump 190 and into the drum 106 for subsequent pumping. Alternatively, the controller 128 may selectively open and close the valves to discharge inert gas 184 through the discharge system 100 to purge the piping and valves of the discharge system 100. Still further, the controller 128 may selectively open and close the valves to discharge inert gas 184 through the calibration system 122 which measures the inert gas purge of the discharge system 100.

After the pump system 114 has emptied the chemical 104 from the drum 106 and stored the chemical 104 in the plurality of storage tanks 224, the worker positions hands through ports 40 and then safely, efficiently, and economically decouples the outlet port 146 from the pump inlet 192 and the inlet port 144 from the second inlet 186. The door 136 is opened and the worker conveniently moves the drum retainer 108 and now empty drum 106 along the second conveyor 158, through the door 136, and onto the first conveyor 156 for subsequent loading on the cargo transport.

Figure 4:
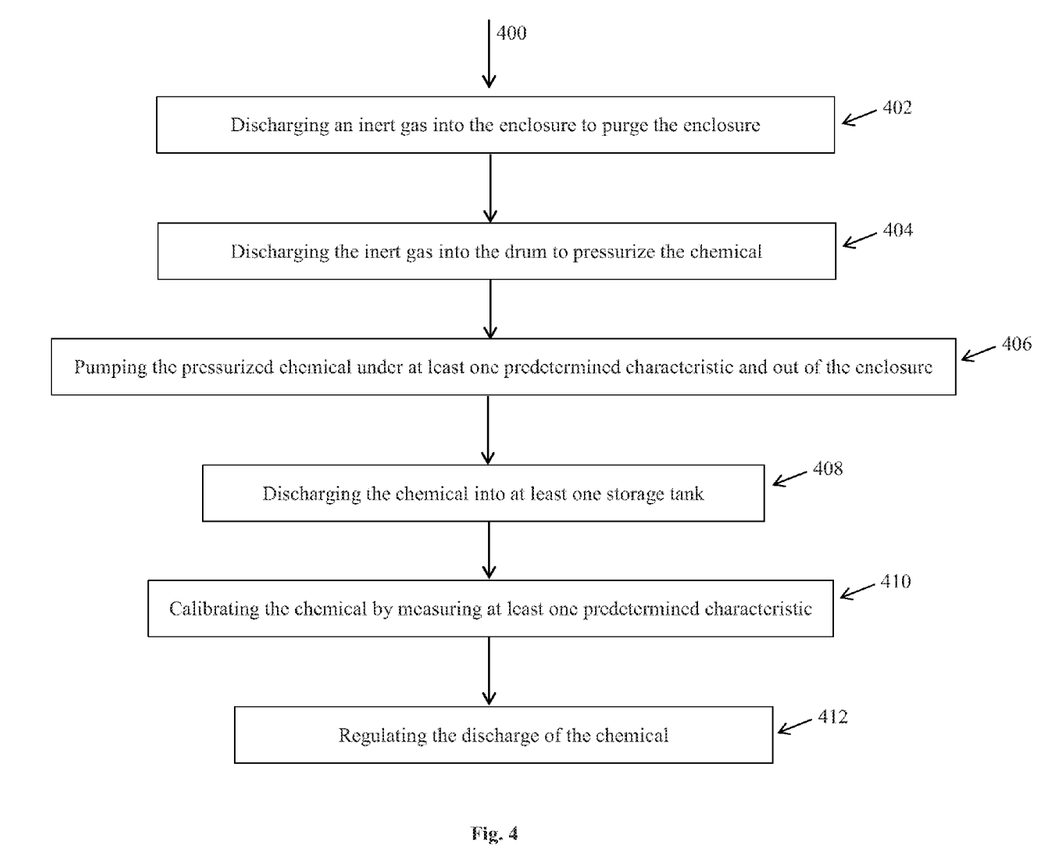
FIG. 4 is an exemplary flowchart illustrating a method of operating steps for operating the chemical discharge system shown in FIG. 1.

FIG. 4 is a flowchart illustrating a method 400 of operating the chemical discharge system 100 by the control system 126. The method 400 includes moving the drum 106 and the drum retainer 108 from the cargo transport and on to the first conveyor 156. The first conveyor 156 moves the drum 106 and drum retainer 108 through the door 136 and on to the second conveyor 158 to position the drum 106 and drum retainer 108 within the enclosure 142. The door 136 is closed and the inlet port 144 is connected to the outlet piping 198. Moreover, the outlet port 146 is connected to the inlet piping 196.

The controller 128 selectively operates valves to discharge the inert gas 184 from the gas header 176 and through the primary gas source 178. The primary gas source 178 discharges 402 the inert gas 184 through the first gas inlet 182 and into the enclosure 142 to facilitate purging the enclosure 142. Moreover, discharging the inert gas 184 into the enclosure 142 facilitates pressurizing the enclosure 142. The blower/fan 176 moves the air, contaminants, and/or the inert gas 184 through the vents 164, across the scrubber 170, and into the atmosphere 174.

During the exemplary method 400, the controller 128 selectively operates valves to discharge the inert gas 184 from the gas header 176 and through the primary gas source 178. The primary gas source 178 discharges the inert gas 184 through the second gas inlet 186 and into the inlet port 144. The method 400 further includes discharging 404 the second inert gas 184 into the drum 106 to pressurize the chemical within the drum 106. The controller 128 selectively operates the pump 190, wherein the chemical 104 is pumped 406, under the at least one predetermined characteristic 200, from the drum 106 and out of the enclosure 142. In the exemplary method 400, the at least one predetermined characteristic 200 includes at least one of the temperature 202 from about 40° F. to about 100° F., the specific gravity 204 from about 1.6 to about 1.7, the flow rate 206 from about 0.5 lb./hr. to about 2000 lb./hr., and the pressure from about 5 psi to about 80 psi of the chemical 104. The method 400 also includes discharging the chemical 104 from the drum 106 and/or through the plurality of branches 214 and/or into the plurality of storage tanks 224 at a flow rate from about 0.5 ft./sec. to about 10 ft./sec. During at least the pumping process, the heat transfer system 120 controls the temperature 202 within the enclosure 142.

The controller 128 continues operation of the pump 190, wherein the chemical 104 is discharged from the outlet port 146 and into at least one branch of the plurality of branches 214. The controller 128 selectively operates the control valves 232 to discharge 408 the chemical 104 through the plurality of branches 214 and selectively into at least one storage tank of the plurality of storage tanks 224. In the exemplary method 400, the chemical is controllably discharged into the storage tank at a flow rate 206 from about 0.5 ft./sec. to about 10 ft./sec. The controller 128 can selectively operate the valves to discharge the inert gas 184 throughout the discharge system 100 to facilitate a pressure balance within the discharge system 100. Additionally, the controller 128 can selectively operate the valves to discharge the inert gas 184 throughout the discharge system 100 to facilitate a backflow purge of components of the discharge system 100. For example, the controller 128 can direct inert gas 184 from the primary gas source 178, through the plurality of branches 214, and through the outlet piping 198. Moreover, the controller 128 can direct inert gas 184 through the pump 190, the inlet piping 196, and through the drum 106 for purging of components. Still further, the controller 128 can direct inert gas 184 through the calibration system 122 which measures and/or calibrates the inert gas backflow purge.

The method 400 includes calibrating 410 the chemical 104 as the chemical 104 is discharged from the drum 106. In the exemplary method 400, the calibration includes measuring the at least one predetermined characteristic 200 and the reporting to the controller 128 the measurement of the at least one predetermined characteristic 200. Moreover, the method 500 includes regulating 412, by the controller 128, the discharge of the chemical 104 that is discharged from the drum 106.

Figure 5:
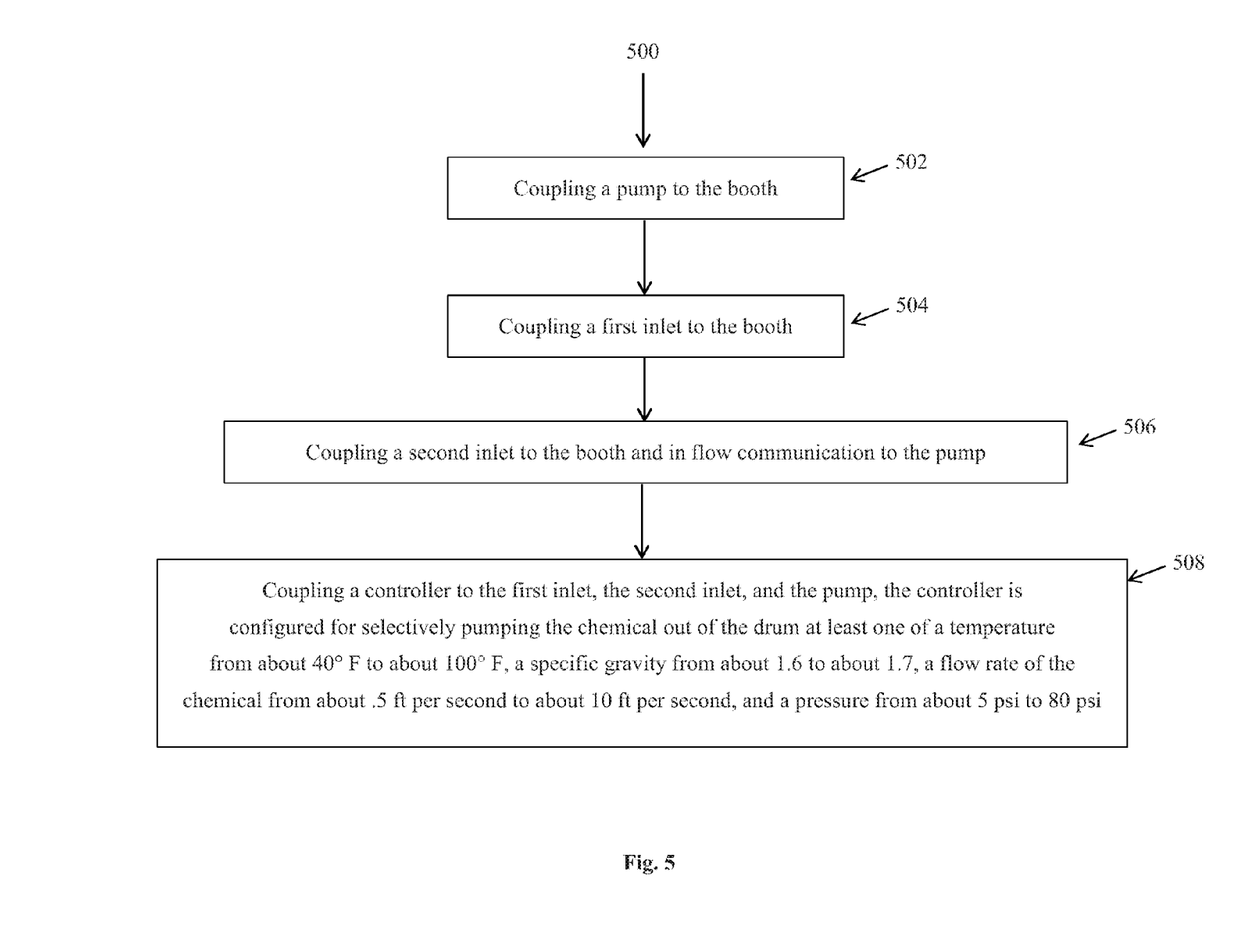
FIG. 5 is an exemplary flowchart illustrating a method of assembly steps for assembling the chemical discharge system shown in FIG. 1.

FIG. 5 is an exemplary flowchart illustrating a method 500 of assembly steps for assembling the chemical discharge system 100 shown in FIG. 1. The method 500 includes coupling the booth 110 to the processing facility 102. In the exemplary method 500, the booth 110 is located within or adjacent to the processing facility 102. Alternatively, the booth 110 can be built on a portable platform and moved to the processing facility 102. Accordingly, the booth 110 can be permanently installed to the processing facility 102 or removably installed to the processing facility 102.

The method 500 includes coupling 502 the pump system 114 to the booth 110. In the exemplary method 500, the pump system 114 is coupled to the booth sidewall 134 and suspended above the floor 130 for chemical leakage considerations. Moreover, the calibration system 122 is coupled to the sidewall 134 and suspended from the floor 130 for chemical leakage considerations. The calibration system 122 is further coupled in flow communication to the pump system 114. In the exemplary method 500, heat transfer system 120 and the conveyor system 124 are coupled to the booth 110. Moreover, the exhaust system 116 is coupled to the booth 110 and in flow communication with the enclosure 142.

The primary gas source 178 is coupled in flow communication to the gas header 176. Alternatively, the secondary gas source 180 is coupled to at least one of the gas header 176 and the primary gas source 178. The first inlet 182 is coupled 504 in flow communication to the booth 110 and to the primary gas source 178. The second inlet 186 is coupled 506 to the booth 110 and in flow communication to the pump system 114. Additionally, the second inlet 186 is coupled in flow communication to the primary gas source 178.

In the exemplary method 500, the plurality of branches 214 is coupled in flow communication to the plurality of storage tanks 224. Moreover, the plurality of storage tanks 224 is coupled in flow communication to at least one of the gas header 176, the primary gas source 178, and the secondary gas source 180. The control system 126 is operatively coupled 508 to at least one of the booth 110, the gas system 112, the pump system 114, the calibration system 122, the heat transfer system 120, and the exhaust system 116. The control system 126 is further coupled to the plurality of storage tanks 224. The control system 126 is coupled to facilitate controlling discharge of the chemical 104 from the drum 106 and into the plurality of storage tanks 224 at the predetermined characteristic 200 including at least one of a temperature 202 from about 40° F. to about 100° F., the specific gravity 204 from about 1.6 to about 1.7, the flow rate 206 of the chemical from about 1 ft./s to about 10 ft./s, and the pressure 208 from about 5 psi to about 80 psi. The method 500 also includes facilitating control of discharge of the chemical 104 from the drum 106 and/or through the plurality of branches 214 and/or into the plurality of storage tanks 224 at a flow rate from about 0.5 lb./hr. to about 2000 lb./hr.

In the specification and the claims, reference will be made to a number of terms, which shall be defined to have the following meanings. The singular forms "a", "an", and "the" include plural references unless the context clearly dictates otherwise. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the term "computer" and related terms, e.g., "controller", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein. Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

Processor is no limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as a flash memory. Alternatively, a floppy disk, a compact disc, a read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor. The above examples are exemplary only, and thus are not intended to limit in any way the definition and/or meaning of the term processor.

Exemplary embodiments of a discharge system and methods for operating, controlling, and assembling a discharge system are described herein. The methods and systems are not limited to the specific embodiments described herein, but rather, components of systems and/or steps of the methods may be utilized independently and separately from other components and/or steps described herein. For example, the methods may also be used in combination with other manufacturing systems and methods, and are not limited to practice with only the systems and methods as described herein. Rather, the exemplary embodiment may be implemented and utilized in connection with many other chemical applications.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

The embodiments described herein relate to systems and methods of discharging a chemical. More particularly, the embodiments relate to system and/or apparatus and/or method to safely, efficiently, and economically discharge a volatile chemical into a processing facility. Moreover, the embodiments relate to containing the chemical drum in an enclosure while remaining connected to a drum retainer and minimizing hazardous conditions for the worker. The embodiments described herein are configured to decrease estimating, designing, manufacturing, installation, operation, maintaining, and/or replacement costs for a chemical discharge system; increase safety, efficiency, and convenience, and production of discharging a volatile chemical; safely, efficiently, and economically handle a drum of volatile chemical while remaining coupled to a drum retainer; and, safely, efficiently, and economically discharge a volatile chemical from a contained drum and into a processing facility.

The embodiments described herein to systems and methods of discharging a chemical at predetermined characteristics such as temperature, pressure, specific gravity, and flow rates. The predetermined characteristic facilitates maintaining a safe, efficient, and economical discharge of the chemical from the drum and/or through the plurality of branches and/or into the plurality of storage tanks. Moreover, the predetermined characteristic facilitates discharging the chemical into the plurality of storage tanks under controlled parameters to increase safety, consistency, and awareness of the chemical being discharged into a storage tank.

A technical effect of the systems and methods described herein include at least one of: (a) decreasing estimating, designing, manufacturing, installation, operation, maintaining, and/or replacement costs for a chemical discharge system; (b) increasing safety, efficiency, and convenience, and production of discharging a volatile chemical; (c) safely, efficiently, and economically handling a drum of volatile chemical while remaining coupled to a drum retainer; and, (d) safely, efficiently, and economically discharging a volatile chemical from a contained drum and into a processing facility.

This written description uses examples to disclose the embodiments, including the best mode, and also to enable any person skilled in the art to practice the disclosure, including making and using any devices or systems and performing any incorporated methods. The patentable scope of the embodiments is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed:

1. A system for discharging a chemical from a drum that is coupled to a drum retainer, the system comprising:
   a booth having a floor, a ceiling, and walls defining an enclosure therein and configured to enclose the drum and the drum retainer;
   a first gas source coupled to the booth and in flow communication to the enclosure and configured to discharge a first inert gas into the enclosure;
   a second gas source coupled in flow communication to the drum and configured to discharge a second inert gas into the drum and to pressurize the chemical;
   a pump coupled in flow communication to the drum and configured to discharge the chemical from the drum under at least one predetermined characteristic and out of the enclosure; and
   a controller coupled to at least one of the first gas source, the second gas source, and the pump wherein the controller is configured to selectively operate the at least one of the first gas source, the second gas source, and the pump.

2. The system of claim 1, wherein the first gas source is configured to discharge the first inert gas into the enclosure and at a pressure range from about 1 pound per square inch (psi) to about 5 psi.

3. The system of claim 1, wherein the second gas source is configured to discharge the second inert gas into the drum and at a pressure range from about 1 psi to about 10 psi.

4. The system of claim 1, wherein the at least one predetermined characteristic of the chemical comprises at least one of a temperature, a specific gravity, a flow rate, and a pressure of the chemical.

5. The system of claim 1, wherein the at least one predetermined characteristic comprises a temperature of the chemical having a range from about 40° F. to about 100° F.

6. The system of claim 1, wherein the at least one predetermined characteristic comprises a specific gravity of the chemical having a range from about 1.6 to about 1.7.

7. The system of claim 1, wherein the at least one predetermined characteristic comprises a flow rate of the chemical having a range from about 0.5 lb./hr. to about 2000 lb./hr.

8. The system of claim 1, wherein the at least one predetermined characteristic comprises a pressure of the chemical having a range from about 5 pounds per square inch to about 80 pounds per square inch.

9. The system of claim 1 further comprising a removable gas source coupled in flow communication to the booth.

10. The system of claim 1 further comprising a conveyor system coupled to the booth.

11. The system of claim 1 further comprising a heat transfer device coupled to the booth.

12. The system of claim 1 further comprising a calibration system coupled to the booth and in flow communication to the pump.

13. A computer-implemented method for discharging a chemical stored in a drum which is coupled to a drum retainer which is positioned in an enclosure, the method implemented using a controller in communication with a memory, the method comprising:
discharging from a first gas source a first inert gas into the enclosure to purge the enclosure;
discharging from a second gas source a second inert gas into the drum to pressurize the chemical;
pumping by a pump the pressurized chemical under at least one predetermined characteristic and out of the enclosure; and wherein the controller is coupled to at least one of the first gas source, the second gas source, and the pump wherein the controller is configured to selectively operate the at least one of the first gas source, the second gas source, and the pump.

14. The computer-implemented method of claim 13, wherein discharging the second inert gas comprises discharging the second inert gas comprising the same composition as the first inert gas.

15. The computer-implemented method of claim 13 further comprising discharging the chemical into at least one storage tank at a flow rate having a range from about 0.5 lb./hr. to about 2000 lb./hr.

16. The computer-implemented method of claim 13 further comprising calibrating the chemical by measuring the at least one predetermined characteristic.

17. The computer-implemented method of claim 13 further comprising selectively controlling the at least one predetermined characteristic comprising at least one of a temperature from about 40° F. to about 100° F., a specific gravity from about 1.6 to about 1.7, a flow rate of the chemical from about 0.5 lb./hr. to about 2000 lb./hr., and a pressure from about 5 psi to about 80 psi of the chemical.

18. A method of manufacturing a discharge system for discharging a chemical from the drum that is coupled to a drum retainer that is positioned within a booth, the method comprising:
coupling a pump to the booth;
coupling a first gas inlet to the booth;
coupling a second gas inlet to the booth and in flow communication to the pump; and
coupling a controller to the first gas inlet, the second gas inlet, and the pump and configured for selectively pumping the chemical out of the drum at least one of a temperature from about 40° F. to about 100° F., a specific gravity from about 1.6 to about 1.7, a flow rate of the chemical from about 0.5 lb./hr. to about 2000 lb./hr., and a pressure from about 5 psi to about 80 psi wherein the controller is configured to selectively operate the first gas inlet, the second gas inlet, and the pump.

19. The method of claim 18 further comprising coupling a calibration system to the booth and in flow communication to the pump.

* * * * *